US00PP15693P2

(12) United States Plant Patent
Larsen

(10) Patent No.: US PP15,693 P2
(45) Date of Patent: Mar. 22, 2005

(54) ***OSTEOSPERMUM* PLANT NAMED 'SUNNY SERENA'**

(50) Latin Name: *Osteospermum ecklonis*
Varietal Denomination: Sunny Serena

(76) Inventor: Bjarne Nyholm Larsen, Grönnegyden 148, DK-5270 Odense N (DK)

( * ) Notice: Subject to any disclaimer, the term of this patent is extended or adjusted under 35 U.S.C. 154(b) by 0 days.

(21) Appl. No.: 10/783,352

(22) Filed: Feb. 21, 2004

(51) Int. Cl.[7] ..... A01H 5/00
(52) U.S. Cl. ..... Plt./360
(58) Field of Search ..... Plt./360

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Osteospermum* plant named 'Sunny Serena', characterized by its compact, upright and mounded plant habit; dense and bushy growth habit; freely flowering habit; and pale yellow-colored ray florets and gray-colored disc florets.

2 Drawing Sheets

Botanical classification/cultivar designation: *Osteospermum ecklonis* cultivar Sunny Serena.

BACKGROUND OF THE INVENTION

The present Invention relates to a new and distinct cultivar of *Osteospermum* plant, botanically known as *Osteospermum ecklonis,* and hereinafter referred to by the name 'Sunny Serena'.

The new *Osteospermum* is a product of a planned breeding program conducted by the Inventor in Odense, Denmark. The objective of the breeding program is to create new compact *Osteospermums* with continuous flowering, good postproduction longevity and attractive flower coloration.

The new *Osteospermum* originated from a cross-pollination made by the Inventor in May, 1998 of the *Osteospermum ecklonis* cultivar Sunny Alex, not patented, as the female, or seed, parent with the *Osteospermum ecklonis* cultivar Sunny Martha, disclosed in U.S. Plant Pat. No. 10,978, as the male, or pollen, parent.

The new *Osteospermum* was discovered and selected by the Inventor as a single flowering plant within the resulting progeny from the cross-pollination in a controlled environment in Odense, Denmark in June, 2000.

Asexual reproduction of the new *Osteospermum* by terminal vegetative cuttings was first conducted in Odense, Denmark. Asexual reproduction by cuttings has shown that the unique features of this new *Osteospermum* are stable and reproduced true to type in successive generations.

SUMMARY OF THE INVENTION

The cultivar Sunny Serena has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sunny Serena'. These characteristics in combination distinguish 'Sunny Serena' as a new and distinct *Osteospermum:*

1. Compact, upright and mounded plant habit.
2. Dense and bushy growth habit.

3. Freely flowering habit.
4. Pale yellow-colored ray florets and gray-colored disc florets.

Plants of the new *Osteospermum* are most similar to plants of the parents, the cultivars Sunny Alex and Sunny Martha. Plants of the new *Osteospermum* differ primarily from plants of the cultivars Sunny Alex and Sunny Martha, in ray floret coloration as ray florets of plants of the cultivars Sunny Alex and Sunny Martha are yellow and purple in color, respectively.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph on the first sheet comprises a side perspective view of a typical flowering plant of 'Sunny Serena' grown in a container.

The photograph on the second sheet is a top perspective view of a typical flowering plant of 'Sunny Serena' grown in a container.

DETAILED BOTANICAL DESCRIPTION

The aforementioned photographs and following observations and measurements describe plants grown in Fyn, Denmark, in a glass-covered greenhouse during the winter and spring. After planting rooted cuttings, plants were grown for about 20 weeks in 11-cm containers. During the first five weeks of production of the plants, day and night temperature were about 20° C., then temperatures were reduced to 14° C. Color references are made to The Royal Horticultural Society Colour Chart, 4$^{th}$ Edition, except where general terms of ordinary dictionary significance are used.

Botanical classification: *Osteospermum ecklonis* cultivar Sunny Serena.

Parentage:

*Female, or seed, parent.*—*Osteospermum ecklonis* cultivar Sunny Alex, not patented.

*Male, or pollen, parent.*—*Osteospermum ecklonis* cultivar Sunny Martha, disclosed in U.S. Plant Pat. No. 10,978.

Propagation:

*Type.*—Terminal vegetative cuttings.

*Time to initiate rooting.*—About 10 to 14 days at 18 to 21° C.

*Root description.*—Fine, fibrous and branching.

Plant description:

*Appearance.*—Perennial herbaceous container and garden plant. Compact, upright and mounded plant habit. Freely branching; dense and bushy growth habit. Vigorous growth rate.

*Plant height.*—About 17 cm.

*Plant width or area of spread.*—About 17 cm.

*Lateral branches.*—Quantity per plant: About four primary lateral branches and about seven secondary lateral branches. Length, primary branches: About 3 cm. Length, secondary branches: About 7 to 12 cm. Diameter, primary and secondary branches: About 4 to 5 mm. Internode length: About 3 mm. Aspect: Mostly upright to about 10 to 20° from vertical. Strength: Strong, sturdy. Texture: Smooth, glabrous. Color: 144C.

*Foliage description.*—Arrangement: Alternate; simple. Length: About 2 to 4 cm. Width: About 1 to 3 cm. Shape: Obovate to spatulate. Apex: Obtuse. Base: Attenuate. Margin: Broadly serrate. Venation pattern: Pinnate. Texture, upper and lower surfaces: Pubescent; scattered short, stiff hairs. Color: Developing foliage, upper surface: 147A. Developing foliage, lower surface: 148C. Fully expanded foliage, upper surface: 139B. Fully expanded foliage, lower surface: 147A. Venation, upper surface: 147C. Venation, lower surface: 148B. Petiole: Length: About 1 to 2 cm. Diameter: About 2 to 4 mm. Texture, upper and lower surfaces: Smooth. Color, upper and lower surfaces: 145B.

Inflorescence description:

*Appearance.*—Terminal and axillary inflorescences held above and beyond the foliage on strong and sturdy peduncles. Composite inflorescence form, radially symmetrical, with elliptic to lanceolate-shaped ray florets and disc florets massed at the center; ray and disc florets develop acropetally on a capitulum. Inflorescences not persistent. Inflorescences face mostly upright to about 10° from vertical.

*Flowering response.*—Plants flower continuous and freely from the spring through the fall in Denmark.

*Postproduction longevity.*—Inflorescences maintain good color and substances for about five to ten days on the plant.

*Quantity of inflorescences per plant.*—Freely flowering; about 13 to 30 buds and open inflorescences.

*Fragrance.*—Faint; fresh, lemon-like.

*Inflorescence diameter.*—About 6 to 7 cm.

*Inflorescence height.*—About 6 mm.

*Disc diameter.*—About 1.5 cm.

*Inflorescence buds.*—Length: About 1.2 cm. Diameter: About 1 cm. Shape: Globular. Color: Towards the base, 145C; towards the apex, 154B.

*Ray florets.*—Length: About 2.5 to 2.8 cm. Width: About 8 mm. Shape: Elliptic to lanceolate. Apex: Acute. Base: Rounded, slightly emargination. Margin: Entire. Texture, upper and lower surfaces: Smooth, glabrous. Orientation: Initially upright then about 60° from vertical. Number of ray florets per inflorescence: About 18 in one whorl. Color: When opening, upper surface: Towards the apex, 160A; towards the base, 158C. When opening, lower surface: Ground color, 162A, with longitudinal stripes, 163D. Fully opened, upper surface: Towards the apex, 10A; towards the base, 158D. Fully opened, lower surface: Ground color, 162A, with longitudinal stripes, 163D.

*Disc florets.*—Shape: Tubular, elongated. Apex: Five-pointed. Length: About 6 mm. Width: At apex, about 2 mm; at base, about 1 mm. Number of disc florets per inflorescence: About 50. Color, immature: 201A. Color, mature: 156A.

*Phyllaries.*—Quantity per inflorescence: About 15. Length: About 6 to 12 mm. Width: About 1 to 3 mm. Shape: Lanceolate. Apex: Acuminate. Base: Fused. Margin: Entire. Color, upper and lower surfaces: 137D.

*Peduncles.*—Length: About 5 to 7 cm. Diameter: About 2 mm. Strength: Strong; sturdy. Texture: Smooth, glabrous. Color: 144C.

*Reproductive organs.*—Androecium: Present on disc florets only. Stamen number: Five per floret; fused around style. Anther shape: Linear. Anther length: About 2 mm. Anther color: N99B. Pollen amount: Abundant. Pollen color: N25A. Gynoecium: Present on disc and ray florets. Pistil number: One per floret. Pistil length: About 4 mm. Pistil color: N187A. Style length: About 2 mm. Stigma shape: Two-parted. Stigma color: N187A. Ovary color: 2D.

*Seed.*—Length: About 2 to 3 mm. Diameter: About 1 mm.

Disease/pest resistance: Resistance to pathogens and pests common to *Osteospermums* has not been observed on plants grown under commercial greenhouse or outdoor conditions.

Weather tolerance: Plants of the new *Osteospermum* have been observed to tolerate drought, rain, wind, and temperatures from about 1 to 35° C.

It is claimed:

1. A new and distinct cultivar of *Osteospermum* plant named 'Sunny Serena', as illustrated and described.

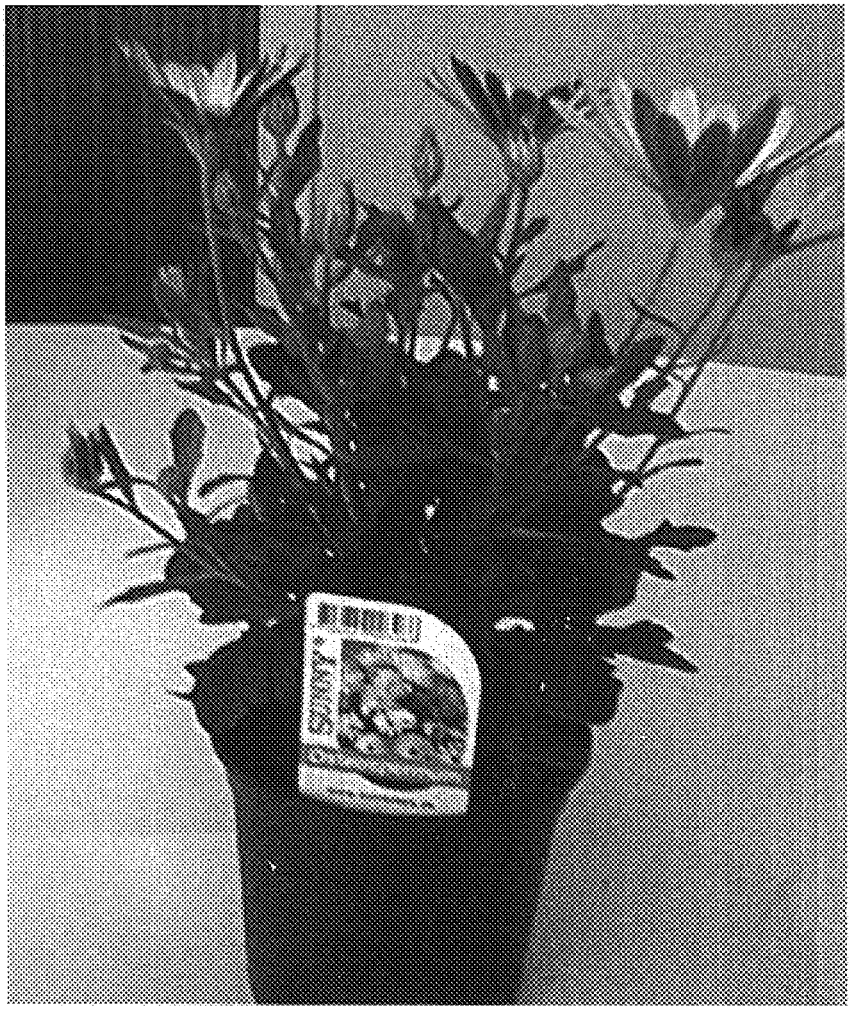

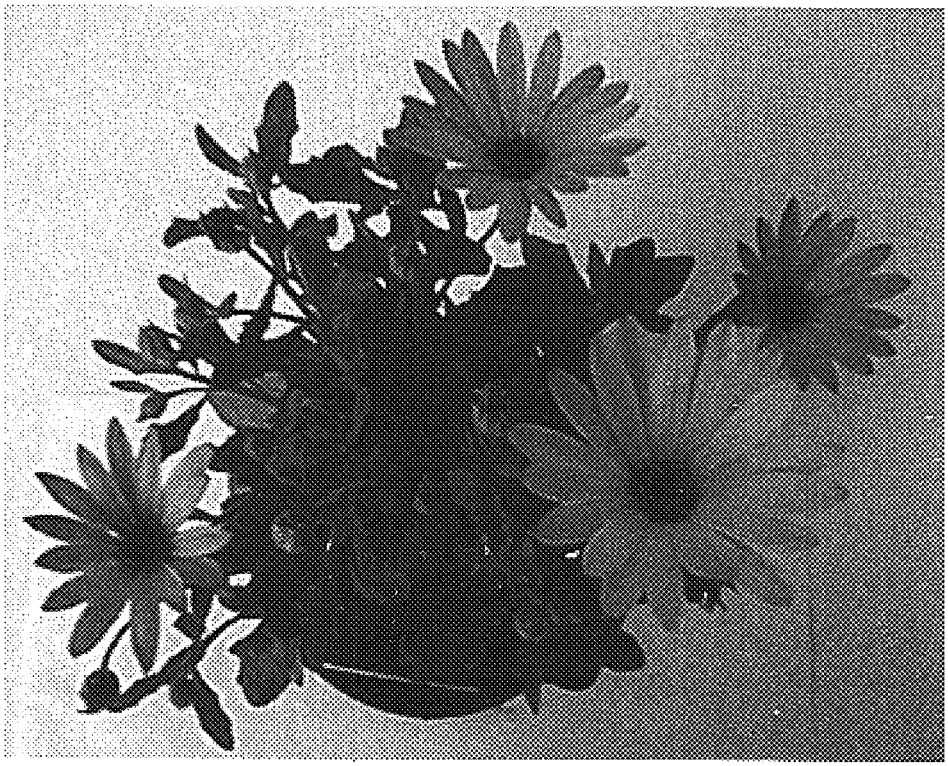

* * * * *